(12) United States Patent
Lee et al.

(10) Patent No.: US 8,604,127 B2
(45) Date of Patent: Dec. 10, 2013

(54) CONJUGATE OF CATECHOL-MODIFIED POLYETHYLENE GLYCOL WITH PROTEIN OR PEPTIDE AND PREPARATION METHOD THEREOF

(75) Inventors: Haeshin Lee, Daejeon (KR); Hyukjin Lee, Daejeon (KR); In Taek Song, Seoul (KR); Moon Sue Lee, Seoul (KR)

(73) Assignees: Korea Advanced Institute of Science and Technology, Daejeon (KR); Inno Therapy Inc., Seoul (KR)

( * ) Notice: Subject to any disclaimer, the term of this patent is extended or adjusted under 35 U.S.C. 154(b) by 0 days.

(21) Appl. No.: 13/133,166

(22) PCT Filed: Oct. 29, 2010

(86) PCT No.: PCT/KR2010/007567
§ 371 (c)(1),
(2), (4) Date: Aug. 9, 2011

(87) PCT Pub. No.: WO2011/053065
PCT Pub. Date: May 5, 2011

(65) Prior Publication Data
US 2012/0208258 A1 Aug. 16, 2012

(30) Foreign Application Priority Data
Oct. 29, 2009 (KR) .................. 10-2009-0103662

(51) Int. Cl.
*A61K 47/48* (2006.01)

(52) U.S. Cl.
USPC ............ 525/54.1; 424/179.1; 424/193.1; 424/194.1; 424/195.11; 525/403; 525/408; 525/430; 528/406; 528/421; 528/492; 528/495; 530/345; 530/402; 530/409; 530/410

(58) Field of Classification Search
USPC ............ 424/179.1, 193.1, 194.1, 195.11; 525/54.1, 403, 408, 430; 528/406, 421, 528/492, 495; 530/345, 402, 409, 410
See application file for complete search history.

(56) References Cited

U.S. PATENT DOCUMENTS

| | | | | |
|---|---|---|---|---|
| 6,506,730 B1 * | 1/2003 | Lee et al. | ............ | 514/11.9 |
| 2009/0093610 A1 * | 4/2009 | Textor et al. | ............ | 528/363 |
| 2010/0137903 A1 * | 6/2010 | Lee et al. | ............ | 606/213 |

OTHER PUBLICATIONS

Canfield, Robert E., The Amino Acid Sequence of Egg White Lysozyme, The Journal of Biological Chemistry, Aug. 1963, pp. 2698-2707, vol. 238, No. 8.

Esch, Frederick, et al., Primary structure of bovin pituitary basic fibroblast growth factor (FGF) and comparison with the amino-terminal sequence of bovine brain acidic FGF, Proceedings of the National Academy of Sciences, Oct. 1985, pp. 6507-6511, vol. 82.

Cohen, Stanley, Isolation of a Mouse Submaxillary Gland Protein Accelerating Incisor Eruption and Eyelid Opening in the New-born Animal, The Journal of Biological Chemistry, May 1962, pp. 1555-1562, vol. 237, No. 5.

Metcalf, D., the granulocyte-macrophage colony-stimulating factors, Science, Jul. 5, 1985, pp. 16-22, vol. 229, No. 4708.

Pasut, G., et al., Polymer-drug conjugation, recent achievements and general strategies, Progress in Polymer Science, Sep. 2007, pp. 933-961, vol. 32.

Veronese, Francesco M., Peptide and protein PEGlation: a review of problems and solutions, Biomaterials, Mar. 1, 2001, pp. 405-417, vol. 22.

Bailon, Pascal, et al., Polyethylene glycol-conjugated pharmaceutical proteins, Pharmaceutical Science & Technology Today, Nov. 1, 1998, pp. 352-356, vol. 1.

Kim, Tae Hyoung, et al. Pegylated recombinant human epidermal growth factor (rhEGF) for sustained release from biodegradabel PLGA microsphere, Biomaterials, 2002, pp. 2311-2317, vol. 23.

Lee, Haeshin, et al., Preparation and Characterization of Mono-PEGylated Epidermal Growth Factor: Evaluation of in Vitro Biological Activity, Pharmaceutical Research, 2002, pp. 845-851, vol. 19, No. 6.

Lee, Haeshin, et al., Single-molecule mechanics of mussel adhesion, Proceedings of the National Academy of Sciences, Aug. 29, 2006, pp. 12999-13003, vol. 103, No. 35.

Lee, H., et al., Mussel-Inspired Surface Chemistry for Multifunctional Coatings, Science, Oct. 19, 2007, pp. 426-430, vol. 318.

Lee, Haeshin, et al., Facile Conjugation of Biomolecules onto Surfaces via Mussel Adhesive Protein Inspired Coatings, Advanced Materials, Jan. 26, 2009, pp. 431-434, vol. 21.

* cited by examiner

*Primary Examiner* — Robert Jones, Jr.
(74) *Attorney, Agent, or Firm* — Tristan A. Fuierer; Andrew D. Gerschutz; Moore & Van Allen, PLLC

(57) ABSTRACT

The present invention relates to a conjugate of a protein or peptide with a polyethylene glycol derivative having catechol, wherein the protein or peptide is mono-PEGylated at the N-terminal with the polyethylene glycol derivative, and to a preparation method thereof. According to the invention, the catechol-PEG derivative can be site-specifically conjugated with the N-terminal amine group of a protein or peptide, so that a homogeneous polyethylene glycol-protein or -peptide conjugate can be obtained in high yield. Unlike a prior art conjugate, the conjugate obtained according to the invention allows the decrease in the activity of the protein to be minimized without chemically modifying the protein, and thus the conjugate has an excellent pharmacological effect. Also, because the conjugate is homogeneous, the process for preparing the conjugate can be simplified. Moreover, the conjugate has uniform biological efficacy in vivo and shows strong resistance to hydrolysis and thus a long in vivo duration time. Accordingly, the conjugate has the effect of increasing the in vivo efficacy and stability of the protein drug.

16 Claims, 12 Drawing Sheets

TIME (MIN)

MASS (m/z)

FIG. 10
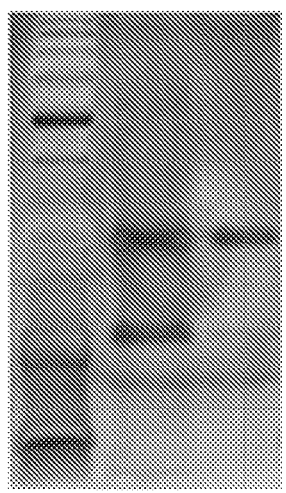
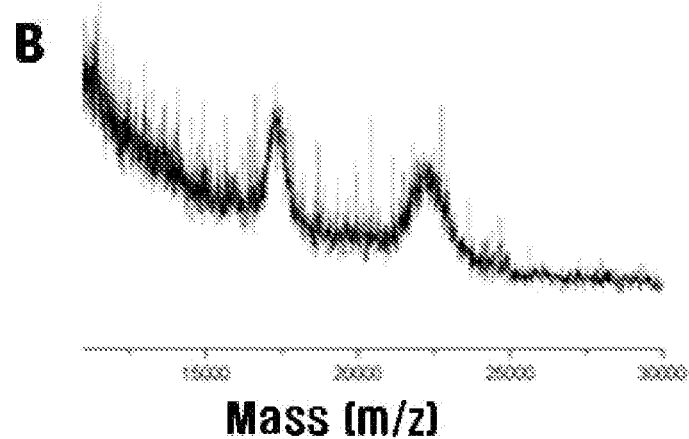
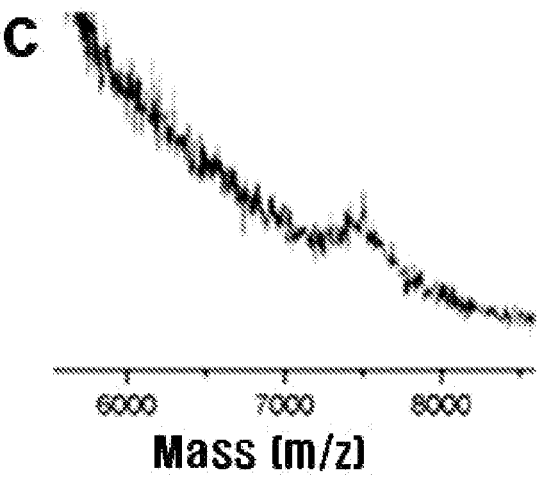

CONJUGATE OF CATECHOL-MODIFIED POLYETHYLENE GLYCOL WITH PROTEIN OR PEPTIDE AND PREPARATION METHOD THEREOF

CROSS-REFERENCE TO RELATED APPLICATIONS

This application is filed under the provisions of 35 U.S.C. §371 and claims the priority of International Patent Application No. PCT/KR2010/007567 filed on 29 Oct. 2010 entitled "Catechol Polyethylene Glycol Derivative and Protein or Peptide Conjugates, and Method for Preparing Same" in the name of Haeshin LEE et al., which claims priority of Korean Patent Application No. 10-2009-0103662 filed on 29 Oct. 2009, both of which are hereby incorporated by reference herein in their entirety.

TECHNICAL FIELD

The present invention relates to a conjugate of a protein or a peptide with a polyethylene glycol derivative having catechol, wherein the protein or the peptide is mono-PEGylated at the N-terminal with the polyethylene glycol derivative, and to a preparation method thereof.

BACKGROUND ART

In the human body, various kinds of proteins or peptides which are involved in the growth and differentiation of the cells are expressed. Such proteins or peptides bind to receptors on the cell wall to induce the expression of various signaling molecules, thereby maintaining the homeostasis of the body. However, if the amount of such proteins or peptides is not maintained at suitable levels in the body, problems associated with homeostasis will arise due to the lack or overexpression of signaling molecules in the body, thus causing various problems. For example, if the level of a human growth hormone or an epidermal growth factor associated with wound healing is low, the body will not grow or the wound will not heal well.

R. Canfield (in the year 1962), F. Esch (in the year 1985), S. Cohen (in the year 1962) and D. Metcalf (in the year 1985) found lysozyme, basic fibroblast growth factor (bFGF), epidermal growth factor (EGF) and granulocyte colony-stimulating factor (G-CSF), respectively, which are protein factors consisting of amino acids, and they also identified the amino acid sequence of each of the protein factors (R. Canfield, *J. Biol. Chem.* 238, 2698, 1963; F. Esch, *Proc. Natl. Acad. Sci. USA* 82, 6507, 1985; S. Cohen, *J. Biol. Chem.* 237, 1555, 1962; D. Metcalf, *Science* 229, 16, 1985).

Such protein factors are known to have effects on would healing (lysozyme/bFGF/EGF) and leukopoiesis (G-CSF), and thus can be used either as therapeutic agents against foot ulcer that is likely to occur in diabetic patients or as therapeutic agents against neutropenia following anticancer therapy.

However, such proteins are known to have a short half-life in blood and tissue. Thus, when these proteins are administered for therapeutic purposes, there is a serious problem in that their in vivo potency and stability are significantly low.

To solve such problems, in recent 10 years, an attempt to conjugate the biocompatible polymer polyethylene glycol (PEG) to proteins or peptides has been continuously made (G. Pasut & F. M. Veronese *Prog. Polym. Sci.* 32, 933, 2007; F. M. Veronese, *Biomaterials* 22, 405.2001; P. Bailon, *Pharm. Sci. Tech. Today* 1, 352, 1998).

Polyethylene glycol (PEG) is a highly biocompatible polymer that does not cause an immune response in vivo and is one of synthetic polymers approved by the US FDA. This synthetic polymer can be used to protein-polyethylene glycol conjugates having increased molecular weights. Thus, these conjugates can keep protein from being cleared by the process of filtration in the kidneys. Also, these conjugates exhibit the effect of inhibiting enzymatic protein degradation in vivo through the stealth effect of polyethylene glycol, thereby increasing the in vivo half-life and stability of the protein. Examples of proteins having increased potency, obtained using this method, include human growth hormone, erythropoietin, interferon, insulin, interleukin, calcitonin, etc.

However, when polyethylene glycol is used to increase the in vivo stability and half-life of a protein drug, there is a problem in that polyethylene glycol reacts with a plurality of binding sites of the protein drug, and thus a heterogeneous mixture of multi-PEGylated species is produced. In particular, the heterogeneous mixture of multi-PEGylated species causes many problems in determining the in vivo half-life and stability of drugs.

Meanwhile, even when a mono-PEGylated conjugate containing one polyethylene glycol molecule bound thereto is prepared under strictly controlled conditions, there is a problem in that the biological or in vivo activity of the drug is significantly influenced by the binding site thereof. To solve this problem, there has been an attempt to conjugate PEG to the N-terminal of proteins or peptides, since the active sites of most therapeutic proteins (EPO, G-CSF, growth hormone, etc.) are not located adjacent to the N-terminal. Specifically, this is because N-terminal PEGylation is a technique capable of minimizing the reduction in protein activation that is the biggest shortcoming of PEGylation.

Thus, to realize the N-terminal site-specific mono-PEGylation as described above, there have been various attempts to site-specifically conjugate mono-polyethylene glycol (mono-PEG) with the primary amine of the N-terminal amine group of proteins or peptides.

The polyethylene glycols used in these prior attempts were methoxypolyethylene glycol derivatives having attached to one end N-hydroxysuccinimide or N-succinimidyl propionate that reacts specifically with the primary amine (T. H. Kim, *Biomaterials,* 23, 2311, 2002; H. Lee, *Pharm. Res.,* 19, 845, 2002). Mono-PEGylated conjugates prepared using succinimide polyethylene glycol derivatives are known to have a very small change in in vivo activity, but N-hydroxysuccinimide or N-succinimidyl propionate is rapidly hydrolyzed during conjugation with proteins or peptides to make it difficult to prepare protein or peptide conjugates, thus reducing the yield of the preparation of the protein or peptide conjugates.

In another attempt to use site-specific protein mutation (single mutation), the technology of performing PEGylation by introducing more than 95% of cysteine into the N-terminal of protein (peptide) drugs has been attempted. However, this technology has a problem in that, because the protein drugs are chemically modified, the bioactivity of the drugs is reduced due to the modification.

In addition, N-terminal specific PEGylation employing aldehyde-PEG was attempted. It is a method applied for the production Neulasta® (Amgen Inc.). However, the reaction conditions in this technology must be limited to acidic conditions (pH 4-6, usually pH 5.0-5.5), and the reducing agent $NaBH_4$ must also be used together. Thus, the application of this technology is limited due to such limited reaction conditions.

Accordingly, the present inventors have found that, if a conjugate of a protein or peptide with a PEG derivative having a compound containing a catechol bound thereto is prepared, a process for preparing the conjugate will be simple, the resulting product will have strong resistance to hydrolysis, and a conjugate comprising a protein or peptide site-specifically mono-PEGylated at the N-terminal primary group can be produced in high yield, thereby completing the present invention.

DISCLOSURE OF INVENTION

The object of the present invention is to provide a conjugate of a protein or a peptide with a polyethylene glycol derivative, wherein the protein or the peptide is mono-PEGylated at the N-terminal amine group with the polyethylene glycol derivative, and a method for preparing the conjugate.

To achieve the above object, the present invention provides a polyethylene glycol derivative having a compound containing a catechol bound thereto, and a conjugate of a protein or a peptide with the polyethylene glycol derivative, wherein the protein or the peptide is mono-PEGylated at the N-terminal with the polyethylene glycol derivative, as well as methods for preparing said polyethylene glycol derivative and conjugate.

BRIEF DESCRIPTION OF THE DRAWINGS

In FIG. 6, peak at minute 13 on the red line: T1 fragment; peak at minute 12 on the red line: the result of insufficient dilution; and peak at minute 23.4 on the red line: PEGylated fragments.

In FIG. 7, a peak appeared at mPEG (MW: 5000) or mPEG plus T1 (MW: 5883).

In FIG. 9, mono-PEGylated catechol-PEG-lysozyme exhibits a single band.

FIG. 10 shows SDS-PAGE results for succinimidyl succinate-PEG-bFGF (lane 2) and catechol-PEG-bFGF (lane 3) (FIG. 10A), MALDI-TOF results for tryptic digests of bFGF (MW: 2495; FIG. 10B), and MALDI-TOF results for tryptic digests of catechol-PEG-bFGF (MW: 7468; FIG. 10C).

FIG. 11B), and MALDI-TOF results for tryptic digests of catechol-PEG-G-CSF (MW: 6792; FIG. 11C).

In FIG. 15, black-line peaks indicate mPEG-CT-EPO (98 minutes) and an EPO mixture (140 minutes), and red-line peaks indicate mono-PEG (105 minutes), di-PEG (98 minutes), and multi-PEG (85 minutes).

BEST MODE FOR CARRYING OUT THE INVENTION

Figure 1:
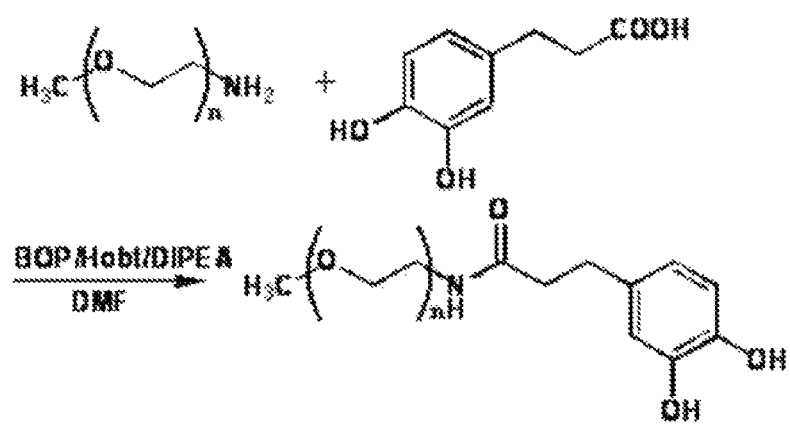
FIG. 1 is a scheme of the reaction of methoxy polyethylene glycol with 3,4-dihydroxycinnamic acid.

The present invention provides a polyethylene glycol derivative having bound thereto a compound containing a catechol of the following formula 1, and a conjugate of a protein or a peptide with the polyethylene glycol derivative, wherein the protein or peptide is site-specifically mono-PEGylated at the N-terminal amine group with the polyethylene glycol derivative:

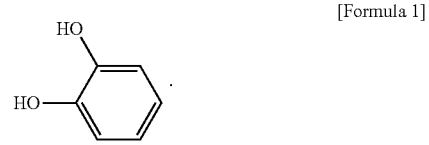

[Formula 1]

The present inventors have conducted studies to solve the above-described problems occurring in the prior art and, as a result, have found a functional group that binds specifically to the N-terminal amine group of proteins, wherein the functional group that is a 3,4-dihydroxy-L-phenylalanine (DOPA) group is known as an amino acid which is abundantly contained in mussel adhesive protein. In studies on dopamine or catechol, a research paper prepared by the present inventors demonstrated that a catechol group can be adsorbed to various surfaces and also that proteins can be coated on various surfaces using this adhesion (H. Lee, *PNAS,* 103, 12999, 2006; H. Lee, *Science,* 318, 426, 2007; H. Lee, *Adv. Mater.* 21, 431, 2009).

Thus, in the present invention, reactive polyethylene glycol derivatives obtained by binding a compound containing a catechol to polyethylene glycol are used. Such polyethylene glycol derivatives can selectively bind to the N-terminal amine group of proteins or peptides, thus forming conjugates, and in this case, the proteins or peptides can be site-specifically mono-PEGylated at the N-terminal with the polyethylene glycol derivatives, thereby preparing protein or peptide formulations that have increased half-life and stability in vivo while maintaining the physiological activity of the proteins or peptides. Also, by using the catechol group which is very stable against hydrolysis that occurs when using derivatives of proteins or peptides, the reaction efficiency can be maintained for a long period of time.

As used herein, the term "polyethylene glycol" is intended to encompass any of the forms of polyethylene glycol (PEG).

The definition thereof also includes derivatives such as methoxy polyethylene glycol aldehyde as described below.

The polyethylene glycol that is used in the present invention is preferably any one selected from the group consisting of, but not limited to, methoxy polyethylene glycol aldehyde, polyethylene glycol succinimidyl propionate, methoxy polyethylene glycol succinimidyl butanoate, methoxy polyethylene glycol succinimidyl succinate, methoxy polyethylene glycol benzotriazole carbonate, methoxy polyethylene glycol epoxide, methoxy polyethylene glycol carbonylimidazole, methoxy polyethylene glycol p-nitrophenyl carbonate, methoxy polyethylene glycol isocyanate, methoxy polyethylene glycol amine containing primary amine, methoxy polyethylene glycol hydrazide, and methoxy carboxyl polyethylene glycol containing carboxyl groups. Because said polyethylene glycol can react with an amine or a carboxyl group, it can bind to a catechol group to form a derivative.

Also, the polyethylene glycol that is used in the present invention may have any shape selected from linear, branch, brush and star-like shapes.

The compound containing a catechol that is used in the present invention is preferably any one selected from the group consisting of, but not limited to, 3,4-dihydroxy-L-phenylalanine containing carboxyl and amine groups, 3-hydroxy-tyramine containing amine groups, 3,4-dihydroxyhydrocinnamic acid containing carboxyl groups, 3,4-dihydroxybenzaldehyde containing aldehyde groups, and norepinephrine. Furthermore, the compound containing a catechol preferably has a molecular weight of 1,000 or less.

The polyethylene glycol derivative according to the present invention preferably has a molecular weight of 500 to 100,000, and more preferably 2,000 to 40,000. This is because it is difficult to obtain a polyethylene glycol derivative having a molecular weight of more than 100,000, and a polyethylene glycol derivative having a molecular weight of less than 500 is present in a liquid state, and thus has poor physical properties leading to low reaction efficiency.

If the polyethylene glycol derivative is conjugated to a protein, a protein-polyethylene glycol derivative conjugate having increased molecular weight can be obtained, and this conjugate can keep the protein from being cleared by the process of filtration in the kidneys. Also, the conjugate exhibits the effect of inhibiting enzymatic protein degradation in vivo through the stealth effect of polyethylene glycol, thereby increasing the in vivo half-life and stability of the protein.

In the present invention, because the protein- or peptide-polyethylene glycol derivative conjugate is prepared by site-specific mono-PEGylation of the protein or peptide as described above, the problem as the production of a heterogeneous conjugate can be prevented. Thus, when the duration of efficacy and stability of a protein or peptide drug according to the present invention is measured, reliable data can be obtained. Also, according to the present invention, a drug having desired in vivo biological activity can be easily prepared. In addition, because the conjugate of the present invention is prepared through N-terminal specific PEGgylation, the pharmacological effect of the protein drug can be maximized without chemically modifying the protein drug.

The protein that is used in the present invention may be any one selected from the group consisting of, but not limited to, lysozyme, basic fibroblast growth hormone (bFGF), granulocyte colony-stimulating factor (GCSF), erythropoientin (EPO), epidermal growth factor (EGF), human growth hormone (hGH), interferon (IFN), interleukin-2 (IL-2), vascular endothelial growth factor (VEGF), luteinizing hormone-releasing hormone (LHRH), growth hormone-releasing hormone (GHRH), mammalian urate oxidase (uricase), and arginine deiminase (ADI). Herein, proteins such as lysozyme, bFGF, EGF and GCSF may be produced using gene recombinant techniques by either extracting these proteins from mammals or cloning these proteins into. DNA vectors and then expressing these proteins in a prokaryotic or eukaryotic host. Herein, examples of the prokaryotic host include *Escherichia coli*, examples of the eukaryotic host include *Hanesnula polymorpha, Saccharomyces cerevisiae*, etc., and the mammals include mice, dogs and pigs.

The peptide that is used in the present invention may be any one selected from the group consisting of, but not limited to, hinge-7, hinge-3, buforin, histonin, protegrin, indolicidin, histatin, BIP, magainin 2, glucagon-like peptide (GLP-1), GNRH/LHRH agonist, somatostatin analogues, immunoregulatory peptide glatiramer, salmon calcitonin, desmopressin, platelet coagulation inhibitory peptides, eptifibatide, and HIV fusion inhibitor enfuvirtide.

The present invention also provides a method for preparing a polyethylene glycol derivative having bound thereto a compound containing a catechol of formula 1, the method comprising the steps of:

(a) dissolving polyethylene glycol in a polar organic solvent in a reactor;

(b) dissolving a crosslinker and a compound, containing a catechol of formula 1, in a polar organic solvent in another reactor;

(c) adding to and reacting with the solution of step (b) N,N-diisopropylethylamine (DIPEA); and (d) adding to and reacting with the solution of step (a) the solution of step (c).

The polyethylene glycol derivative prepared according to above method of the present invention is characterized in that it can be mono-conjugated (mono-PEGylated) with the N-terminal amine group of proteins or peptides.

Hereinafter, each step of the preparation method according to the present invention will be described in detail.

Steps (a) and (b) of the preparation method according to the present invention are steps of preparing solutions of reaction materials. In steps (a) and (b), a polar organic solvent may be used to dissolve the reaction materials. Preferred examples of a polar organic solvent that may be used in the present invention include alcohol, dimethyl sulfoxide (DMSO), dimethyl formaldehyde (DMF), acetone and N-methylpyrrolidone (NMP). Of these solvents, the most preferred is DMF, because DMF can prevent the oxidation of a catechol group.

The crosslinker that is added to the compound containing a catechol may be one or more selected from the group consisting of benzotriazolyloxytris(dimethylamino)phosphonium hexafluorophosphate (BOP), hydroxybenzotriazole (HOBt), ethyl-(N',N'-dimethylamino)propylcarboiimide hydrochloride (EDC), dicyclohexylcarbodiimide (DCC), N-hydroxysuccinimide (NHS) and sodium cyanoborohydride. A preferred example of the crosslinker that is used for the binding of an amine group with a carboxyl group may be a combination of HOBt and BOP, a combination of EDC and NHS, and a combination of DCC and NHS. A preferred example of the crosslinker that is used for the binding of an amine group with an aldehyde group may be sodium cyanoborohydride.

For example, BOP and HOBt are zero-order crosslinkers. In the most preferred embodiment, the molar ratio of BOP:HOBt:compound containing a catechol (Polyehthylene glycol derivative) preferably ranges from 1:1:1 to 10:10:1. If the molar ratio is out of this range, the reactivity between the reaction materials can be reduced.

Step (c) of the preparation method according to the present invention is a step of adding N,N-diisopropylethylamine (DI- PEA) to the catechol-containing solution of step (b) and allowing the mixture to react. In step (c), preferably, the DIPEA is added as an organic base to the catechol-containing solution, and then allowed to react for about 10-20 minutes.

Step (d) of the preparation method according to the present invention is a step of adding the solution of step (c) to the solution of step (a) and allowing the mixture to react. The reaction in step (d) is preferably carried out at room temperature for about 10-14 hours. In one Example of the present invention, it was shown that methoxy polyethylene glycol and the compound containing a catechol were bound to each other in step (d), thereby forming a polyethylene glycol derivative.

Also, the preparation method of the present invention may further comprise step (e) of dialyzing the solution of step (d). Step (e) of the preparation method according to the present invention is a step of dialyzing the solution of step (d) to remove unreacted material, after completion of the reaction. The dialysis is preferably carried out for 10-14 hours using a dialysis membrane having a molecular weight cut-off of 2,000 to 10,000.

Herein, distilled water having a pH of 1-6 is preferably used as a dialysis solution. If the pH of the dialysis solution is out of this range, the oxidation of catechol can undesirably occur.

Also, the preparation method according to the present invention may further comprise step (f) of freeze-drying the dialyzed solution of step (e). Step (f) of the preparation method according to the present invention is a step of freeze-drying the dialyzed solution to obtain a polyethylene glycol derivative as white powder. Step (f) can be carried out by a freeze-drying method known to a person of ordinary skill. Through step (f), the solvent is sublimed, thereby obtaining a polyethylene glycol derivative as white powder. In addition, additional drying may also be carried out to completely remove the solvent.

The present invention also provides a method for preparing a conjugate of a protein or a peptide with a polyethylene glycol derivative, wherein the protein or peptide is mono-PEGylated at the N-terminal amine group with the polyethylene glycol derivative, the method comprising the steps of:

(a) dissolving the polymer or peptide in a reactor;
(b) dissolving the polyethylene glycol derivative in another reactor; and
(c) adding to and reacting with the solution of step (b) the solution of step (a).

Hereinafter, each of the method for preparing the protein- or peptide-polyethylene glycol derivative conjugate according to the present invention will be described in detail.

Step (a) of the conjugate preparation method according to the present invention is a step of dissolving the protein or peptide, having an N-terminal amine group, in the reactor. Preferably, the protein or peptide may be dissolved in a buffer in the reactor. The buffer that is used in step (a) may be any one selected from the group consisting of phosphate buffered saline, imidazole buffer, trimethylamine buffer, triethanolamine buffer, sodium diethylbarbiturate buffer, bicine buffer, and aminomethylpropanediol buffer. Also, the pH of the buffer solution is preferably 5.5 to 10. If the pH of the buffer is lower than 5.5, the reactivity of the protein or peptide will be reduced, and if the pH is higher than 10, the stability of the protein or peptide drug will be reduced.

Step (b) of the conjugate preparation method according to the present invention is a step of dissolving the polyethylene glycol derivative, provided according to the present invention, in another reactor. Preferably, the propylene glycol derivative may be dissolved in the same buffer as used in step (a).

Step (c) of the conjugate preparation method according to the present invention is a step of adding the solution of step (a) to the solution of step (b) and subjecting the solution mixture to a PEGylation reaction. The PEGylation reaction is preferably carried out at 4 to 25° C. for 2 to 100 hours.

In step (c), an oxidizing agent may also be used to increase the activity of the polyethylene glycol derivative. The oxidizing agent that is used in the present invention may be any one or more selected from the group consisting of $NaIO_4$, $MnCl_2$, $FeCl_2$, $FeCl_3$, $KMnO_4$, $H_2O_2$, $Na_2Cr_2O_7$, and $Na_3VO_4$. The oxidizing agent may be added during the dissolution of the polyethylene glycol derivative. The oxidizing agent is preferably used at a molar ratio of 1:1 to 1:10 relative to the polyethylene glycol derivative. In the most preferred embodiment, $NaIO_4$ may be added at a molar ratio of 1.5:1 relative to the catechol group. If the PEGylation reaction time is shorter than 2 hours, the efficiency of conjugation of polyethylene glycol will be reduced, and if the reaction time is longer than 100 hours, the stability of the protein or peptide will be reduced. Also, if the reaction temperature is lower than 4° C., the reaction rate will be too low, and if the reaction temperature is higher than 25° C., the protein or peptide will be modified.

In a preferred embodiment of the present invention, the conjugate preparation method according to the present invention may further comprise, after step (c), step (d) of dialyzing the solution of step (c) and then separating the conjugate from the dialyzed solution. Step (d) of the conjugate preparation method according to the present invention is a step of either dialyzing the solution to remove unreacted material or separating the conjugate through liquid phase chromatography (HPLC or FPLC), after completion of the PEGylation reaction. Step (d) may be carried out using a conventional dialysis method or liquid phase chromatography method known to those of ordinary skill in the art.

EXAMPLES

Hereinafter, the present invention will be described in further detail with reference to examples. It will be obvious to a person having ordinary skill in the art that these embodiments are merely for illustrative purposes, and the scope of the present invention should not be construed as being limited to the above described embodiments.

Example 1

Synthesis of catechol-polyethylene glycol (PEG) Derivative

To synthesize a polyethylene glycol (PEG) derivative having a compound containing a catechol bound thereto, methoxy polyethylene glycol was used as PEG, and 3,4-dihydroxycinnamic acid was used as the compound containing a catechol.

In 15 ml of the polar organic solvent DMF (dimethylformamide) in a reactor, 1000 mg of methoxy-polyethyleneglycol (m-PEG; MW: 5000) having a terminal amine group was allowed to react with 3,4-dihydroxycinnamic acid (HCA), hydroxybenzotrizole (HOBt), benzotriazolyloxytris phosphonium hexafluorophosphate (BOP) and N,N-diisopropylethylamine (DIPEA) for 720 minutes while being stirred. Herein, the amounts of the compounds used were 38 mg, 110 mg and 44 µl. Meanwhile, DMF used as the solvent was advantageous for the reaction, because it could prevent oxidation of catechol group of HCA.

As shown in FIG. 1, the reaction product was dialyzed for 24 hours to remove the remaining unreacted material after completion of the reaction. Then, the resulting material was freeze-dried, thus obtaining 3,4-dihydroxycinnamic acid-PEG as white powder. The obtained material was confirmed to be a PEG derivative (hereinafter referred to as mPEG-CT) having catechol.

Example 2

Preparation of PEG-hinge-3 Conjugate Using mPEG-CT and Examination of Conformation of the Prepared Conjugate (1) Preparation of PEG-hinge-3 Conjugate Using mPEG-CT In order to conjugate a polyethylene glycol derivative with a peptide, mPEG-CT was prepared according to the method of Example 1 (FIG. 1). Namely, mPEG-amine (MW: 5000) and HCA were allowed to react with HOBt, BOP and DIPEA in a DMF solution, thus obtaining mPEG-CT.

Then, the mPEG-CT was allowed to react with hinge-3 peptide (see FIG. 2) at 4° C. under a slightly acidic condition (pH 6.5). As a result, a PEG-hinge-3 conjugate was successfully prepared.

(2) RP-HPLC and MALDI-TOF for Confirming mono-PEGylation

In order to confirm whether the PEG-hinge-3 conjugate prepared in Example 2-(1) has a conformation in which the hinge-3 peptide is mono-PEGylated with PEG, RP-HPLC (reverse phase-high performance liquid chromatography) and MALDI-TOF (Matrix-Assisted Laser Desorption Ionization Time of Flight) were performed.

The HPLC system used was Agilent 1200 series, and the column was supelco Discovery® BIO Wide Pore C18 5 cm*4.6 mm, 3 μm. The mobile phase consisted of water (0.1% TFA): acetonitrile (0.1% TFA)=95:5, water (0.1% TFA): acetonitrile (0.1% TFA)=5:95 (up to 30 minutes), and 95% water (up to 35 minutes).

Figure 3:
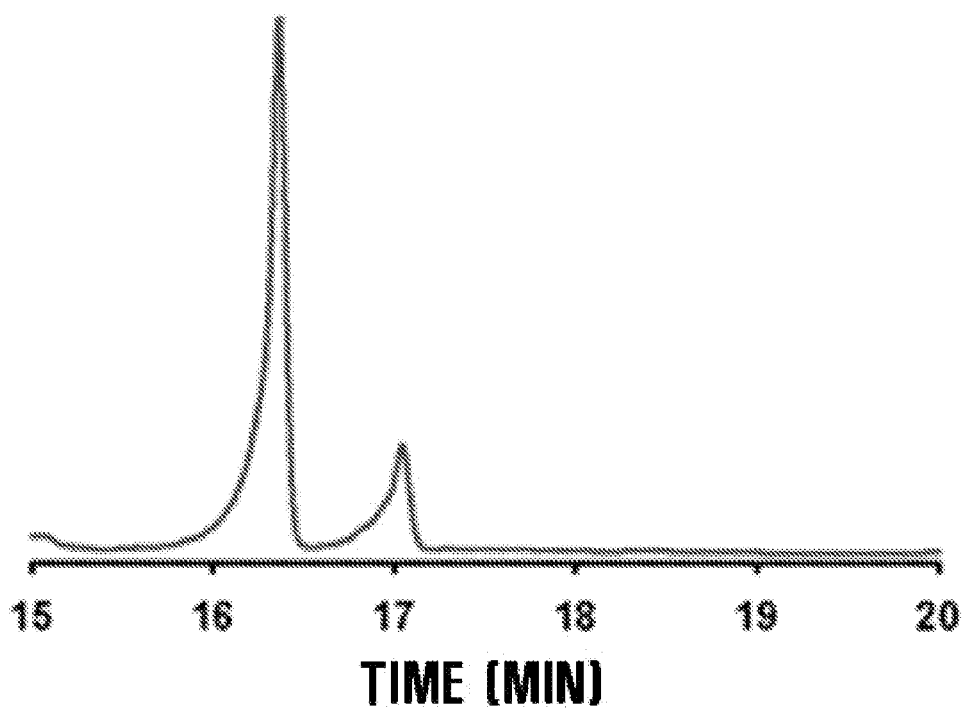
FIG. 3 shows the results of RP-HPLC of a mixture of mPEG-CT with hinge-3.

As a result, as shown in FIG. 3, the results of RP-HPLC showed that only two peaks were detected. The two peaks indicate unmodified hinge-3 (16.2 minutes) and mono-PEGylated hinge-3 (17 minutes), only mono-PEGylation occurred without multi-PEGylation.

For MALDI-ToF analysis, an acetonitrile solution (0.1% trifluoroacetic acid (TFA)) was mixed with water (0.1% trifluoroacetic acid (TFA)) at a ratio of 1:1, and the protein was adsorbed onto the stationary phase using a zip tip, and then washed with water to remove salts from the buffer. Then, only pure PEG-hinge-3 was purified using a 1:1 mixture or acetonitrile and water and placed on a MALDI-ToF plate. Then, the sample was subjected to MALDI-ToF analysis using a Voyager DE-STR system (Applied Biosystems, Inc.).

Figure 4:
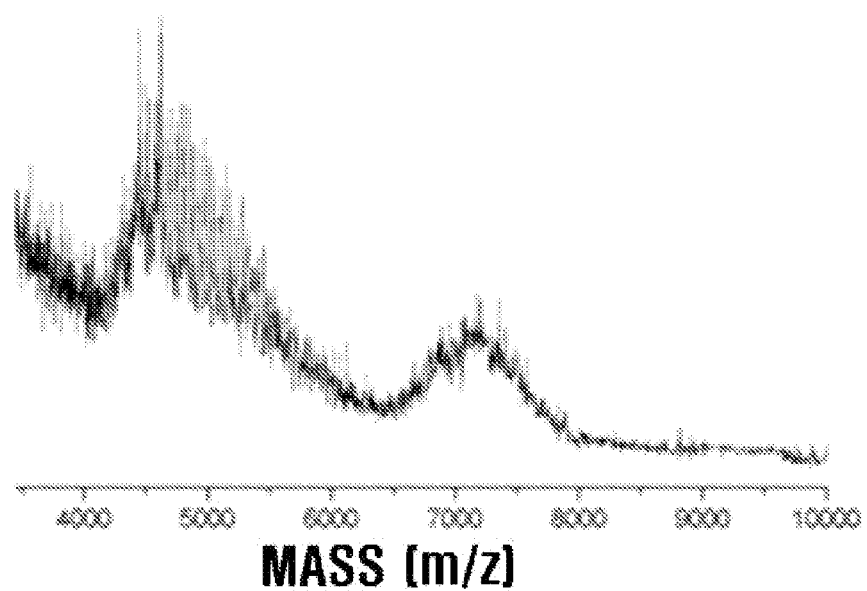
FIG. 4 shows the results of MALDI-TOF of a mixture of mPEG-CT with hinge-3.

As a result, as shown in FIG. 4, the results of MALDI-TOF analysis also showed that only PEG (MW: 5000) and mono-PEG-hinge-3 (MW: 7238) were detected. Thus, it was confirmed that, in the peptide-polyethylene glycol conjugate prepared using the catechol-polyethylene glycol derivative, the peptide was mono-PEGylated with polyethylene glycol.

(3) Examination of mono-PEGylation Sites Through Tryptic Degradation

In order to examine whether the PEG-hinge-3 conjugate prepared in Example 2-(1) has a conformation in which PEG is site-specifically conjugated to the N-terminal of the hing-3 peptide, the conjugate was subjected to tryptic digestion, followed by RP-HPLC and MALDI-ToF analysis.

Figure 2:
FIG. 2 is the amino acid sequence of a hinge-3 peptide.
Figure 5:
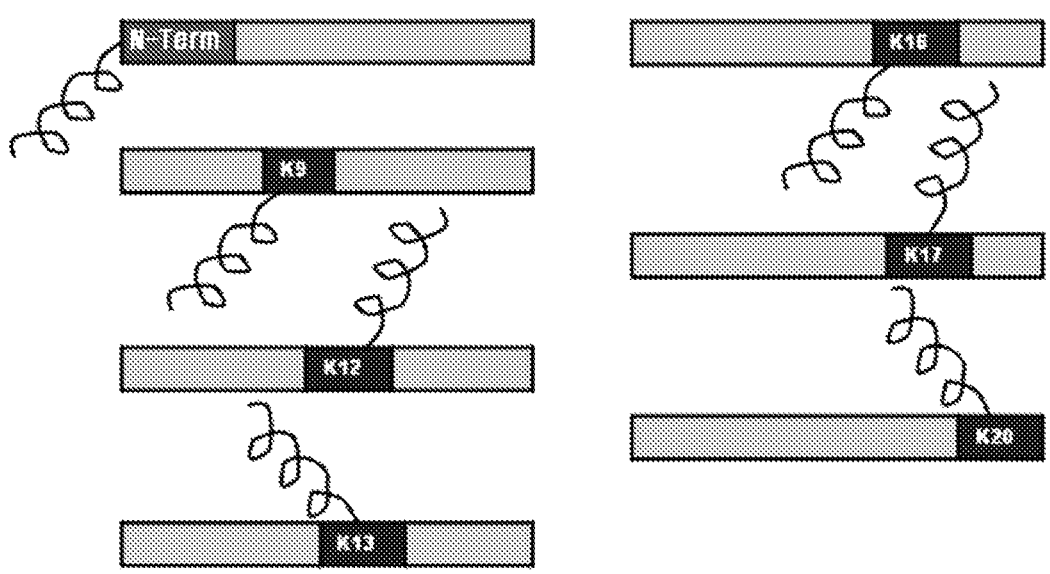
FIG. 5 is a schematic diagram showing PEGylation candidates present in hinge-3.

The peptide, named "hinge-3", has 20 amino acids (see FIG. 2). The peptide has 7 exposed primary amines (potential PEGylation sites), that is, 6 epsilon-amine groups at lysine (K) and one alpha-amine group at the N-terminal. All the amines were candidates for PEGylation sites (see FIG. 5). Accordingly, whether the peptide was PEGylated only at the N-terminal alpha-amine group among these sites was examined. Since the hinge-3 sequence contains only one tryptophan amino acid (see FIG. 2), whether the hinge-3 peptide was PEGylated only at the N-terminal could be examined through the shape of tryptic digests of the peptide.

Since the hinge-3 peptide has no cysteine, a solution of a small amount of calcium chloride ($CaCl_2$) in 4M urea was added to the hinge-3 peptide, and then immediately trypsin was added to the solution in an amount of 1/20 of the peptide. Then, the peptide was subjected to tryptic digestion at 37° C. for 12 hours, followed by RP-HPLC analysis.

Figure 6:
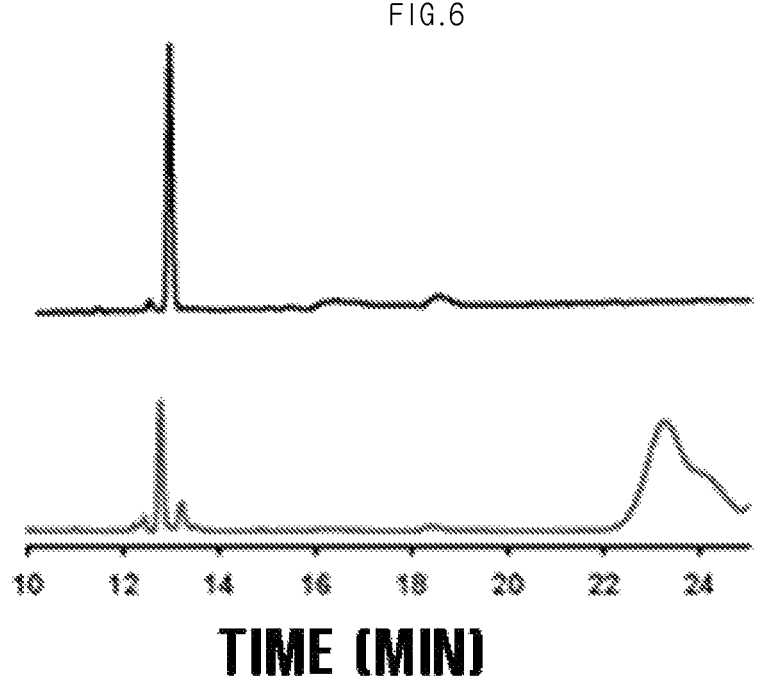
FIG. 6 is a graphic diagram showing RP-HPLC results for tryptic digests of PEG-hinge-3.

As a result, a graph as shown in FIG. 6 was obtained. As can be seen therein, at 280 nm UV, only tryptophan residue was detected. This is because the digested hinge-3 shows a single peak at the T1 fragment (13 min). If catechol reacted with the epsilon amines (K12, K13, K16, K17, and K20), the peak of the single fragment would not change. However, as can be seen from the results in FIG. 6, the peak of the single fragment surely decreased (red line). Namely, due to the catechol group, the intensity of the peak increased only when the T1 fragment existed. The presence of the prior peak (13 min; red line) was because sufficient dilution was not performed (MWCO: diluted at 1:6000).

After the RP-HPLC analysis, only the K9 and N-terminal amines among the PEGylation candidates would remain. If mPEG-CT reacted with K9, the molecular weight of the PEGylated and digested fragments, that is, the mPEG-CT plus T1+2, would be 6254.49, because trypsin could not recognize the PEGylated lysine (K9). Thus, MALDI-ToF analysis was performed in order to examine the site at which mPEG-CT was PEGylated. The MALDI-ToF analysis was performed in the same manner as described in Example 2-(2).

Figure 7:
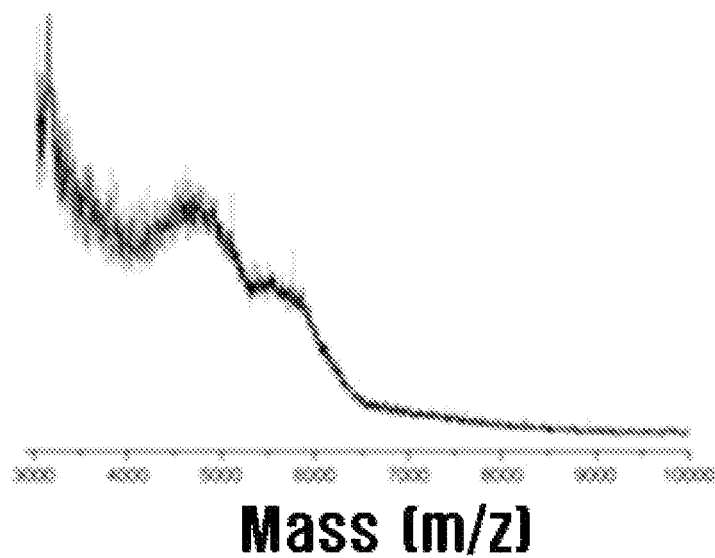
FIG. 7 is a graphic diagram showing the results of MALDI-TOF analysis of tryptic fragments of PEG-hinge-3.

The results of the MALDI-ToF analysis are shown in FIG. 7. As can be seen therein, only two peaks existed: 5000, and 5883. Such results surely indicate that the peak at 5000 is mPEG-CT and the peak at 5883 is mPEG-CT plus the T1 fragment (MW: 899) of hinge-3. The molecular weight of mPEG-CT plus T1+2 fragment (6254.49) was not observed, and thus the peak at 5883 is the reliable evidence of N-terminal PEGylation. Accordingly, it was confirmed that the PEG-hinge-3 conjugated prepared using mPEG-CT in Example 2-(1) has a conformation in which the hinge-3 peptide was mono-PEGylated at the N-terminal.

Example 3

Figure 8:
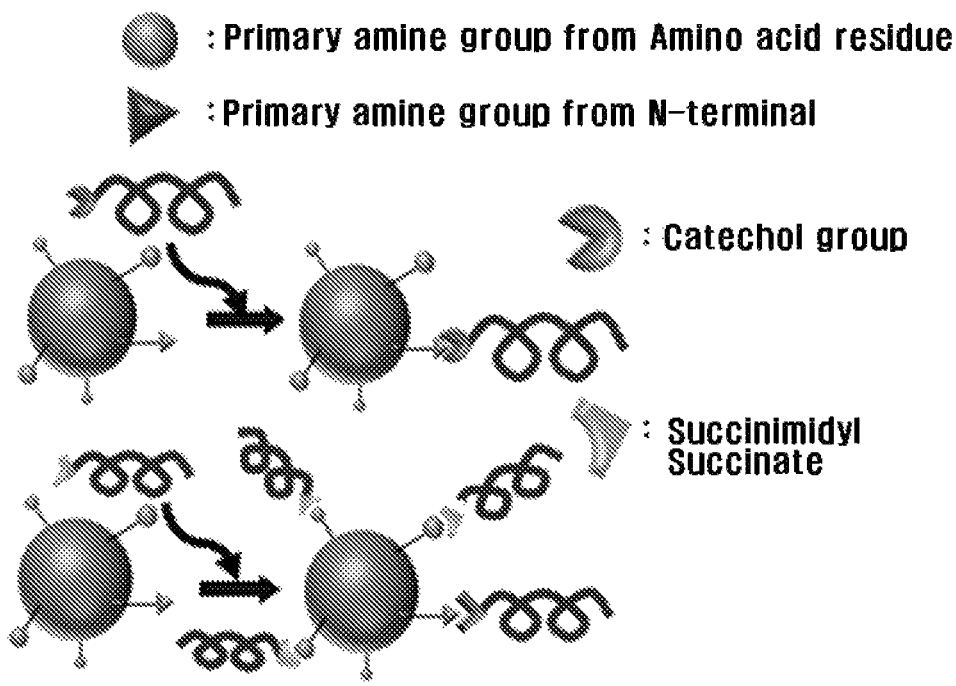
FIG. 8 is a schematic diagram showing the configuration of the binding between a catechol group and succinimidyl succinate.

Comparison with PEG-lysozyme Conjugate Using mPEG-SS and mPEG-CT (1) Preparation of PEG-lysozyme Using mPEG-SS Not only peptide, but also protein may be PEGylated at the N-terminal. In the prior art, the most useful method for amine PEGylation was the use of succinimidyl succinate capable of forming a covalent bond with a surface-exposed primay amine group. However, this method had a problem in that it is not site-specific. This is because succinimidyl succinate reacts with random primary amine groups, unlike a catechol group (FIG. 8). Thus, in order to compare a catechol group with succinimidyl succinate, a PEG-lysozyme conjugate was prepared using mPEG-SS and lysozyme as an example of protein.

Specifically, at a pH of 8.5 which is a generally known condition, 20 mg of mPEG-SS was allowed to react with 5 mg of lysozyme at 4° C. for 12 hours, thus preparing a PEG-lysozyme conjugate.

As a result, it was confirmed that the PEG-lysozyme conjugate was prepared.

(2) Preparation of PEG-lysozyme Conjugate Using mPEG-CT

In order to prepare a PEG-lysozyme conjugate using the mPEG-CT of Example 1, according to the same method described in Example 2-(1), 5 mg of mPEG-CT (5 k) was mixed with 5 mg of lysozyme at a pH of 8.5, and the mixture was allowed to react at 4° C. for 12 hours.

As a result, it was confirmed that a PEG-lysozyme conjugate was prepared.

(3) Examination of mono- or multi-PEGylation Using SDS-PAGE Gel Analysis

The PEG-lysozyme conjugates of Examples 3-(1) and 3-(2) were subjected to SDS-PAGE gel analysis in order to examine whether the conjugates were mono-PEGylated or multi-PEGylated.

For this purpose, a SDS PAGE gel having an acrylamide fraction of 15% was prepared, and a voltage was applied thereto to separate lysozyme and the PEG-lysozyme conjugate according to size.

Figure 9:
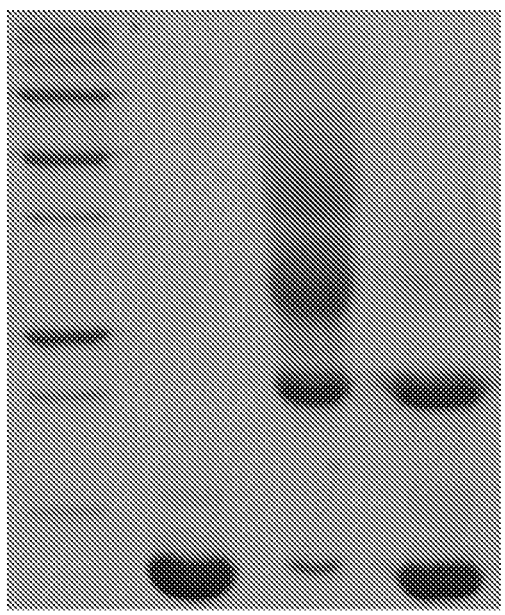
FIG. 9 shows the results of SDS-PAGE of succinimidyl succinate-PEG-lysozyme (lane 3) and catechol-PEG-lysozyme (lane 4).

The results of the analysis are shown in FIG. 9. In FIG. 9, lane 1 is the result of loading lysozyme as a control, lane 2 is the results of loading the PEG-lysozyme conjugate of Example 3-(1), and lane 3 is the results of loading the PEG-lysozyme conjugate of Example 3-(2). As a result, the conjugate of lane 2 prepared using methoxy-polyethylene glycol succinimidyl succinate (mPEG-SS) reacted with three amine groups (3 bands appeared) (K33, K97, and K116). However, as can be seen in lane 3, the PEG-lysozyme conjugate prepared using mPEG-CT showed only one band, suggesting that the conjugate reacted with only one amine group. Thus, it was confirmed that the catechol-PEG derivative was mono-conjugated with the protein, unlike the succinimidyl succinate-PEG derivative.

Example 4

Preparation of PEG-bFGF Conjugate Using mPEG-CT and Examination of Conformation of the Prepared Conjugate (1) Preparation of PEG-bFGF Conjugate Using mPEG-CT or mPEG-SS bFGF (MW: 17.1 kDa) is a basic fibroblast growth factor that is one kind of FGF. In adult organs, it is involved in wound healing and tissue regeneration. According to the same method as used in Example 2-(1), a PEG-bFGF conjugate was prepared using mPEG-CT. As a result, it was confirmed that the PEG-bFGF conjugate was prepared.

Meanwhile, according to the same method as described in Example 3-(1), a PEG-bFGF conjugate was prepared using mPEG-SS.

(2) Examination of mono-PEGylation by SDS PAGE Gel Analysis

The PEG-bFGF was subjected to SDS-PAGE analysis and MALDI-ToF analysis according to the same method as described in Example 2-(2) in order to examine whether the PEG-bFGF was a mono-PEGylated conjugate. However, the analysis was performed at a pH different from the pH value used in Example 2-(2). This is because the N-terminal amine has a different pKa value. Whether bFGF was PEGylated was analyzed at pH 6.5.

The results of the analysis are shown in FIG. 10A.

In FIG. 10A, the protein loaded into lane 2 is the result of performing PEGylation using mPEG-CT at a pH of 6.5, and in lane 2, two bands, that is, the band of the prior bFGF and the band of the mono-PEGylated PEG-bFGF conjugate, could be observed. The protein loaded into lane 3 is a mono-PEGylated PEG-bFGF conjugate obtained by separating and purifying the protein of lane 2 by FPLC. Accordingly, it was confirmed that, when a protein-polyethylene glycol conjugate is prepared using a catechol-polyethylene glycol derivative, the protein is mono-PEGylated with polyethylene glycol.

(3) Examination of PEGylation Sites by Tryptic Digestion

PEGylation sites of the PEG-bFGF were examined by tryptic digestion according to the same method as Example 2-(3)

As a result, as shown in FIG. 10C, the peak of the T1 fragment was observed at 7468. Because the molecular weight of the T1 fragment of unmodified bFGF is 2495 (FIG. 10B), the peak at 7468 is surely the sum of mPEG-CT (MW: 5000) and the T1 fragment of bFGF (MW: 2495), and thus the peak at 7468 is the reliable evidence of N-terminal PEGylation. Accordingly, it was confirmed that the PEG-bFGF prepared using mPEG-CT is a conformation in which the bFGF protein was mono-PEGylated at the N-terminal with PEG.

Example 5

Preparation of PEG-G-CSF Conjugate Using mPEG-CT and Examination of Conformation of the Prepared Conjugate (1) Preparation of PEG-G-CSF Conjugate Using mPEG-CT or mPEG-SS G-CSF (Granulocyte Colony-Stimulating Factor; MW: 18.8 kDa) is the most important protein in the human blood system and serves to stimulate the marrow to be released into the blood flow. A PEG-G-CSF conjugate was prepared according to the same method as Example 2-(1). As a result, it was confirmed that the PEG-G-CSF conjugate was prepared.

Meanwhile, a PEG-G-CSF conjugate was prepared using mPEG-SS according to the same method as Example 3-(1).

(2) Examination of PEGylation by DS-PAGE Gel Analysis

Whether the G-CSF protein was mono-PEGylated was examined by PEG-bFGF analysis and SDS-PAGE gel analysis according to the same method as Example 2-(2).

Figure 11:
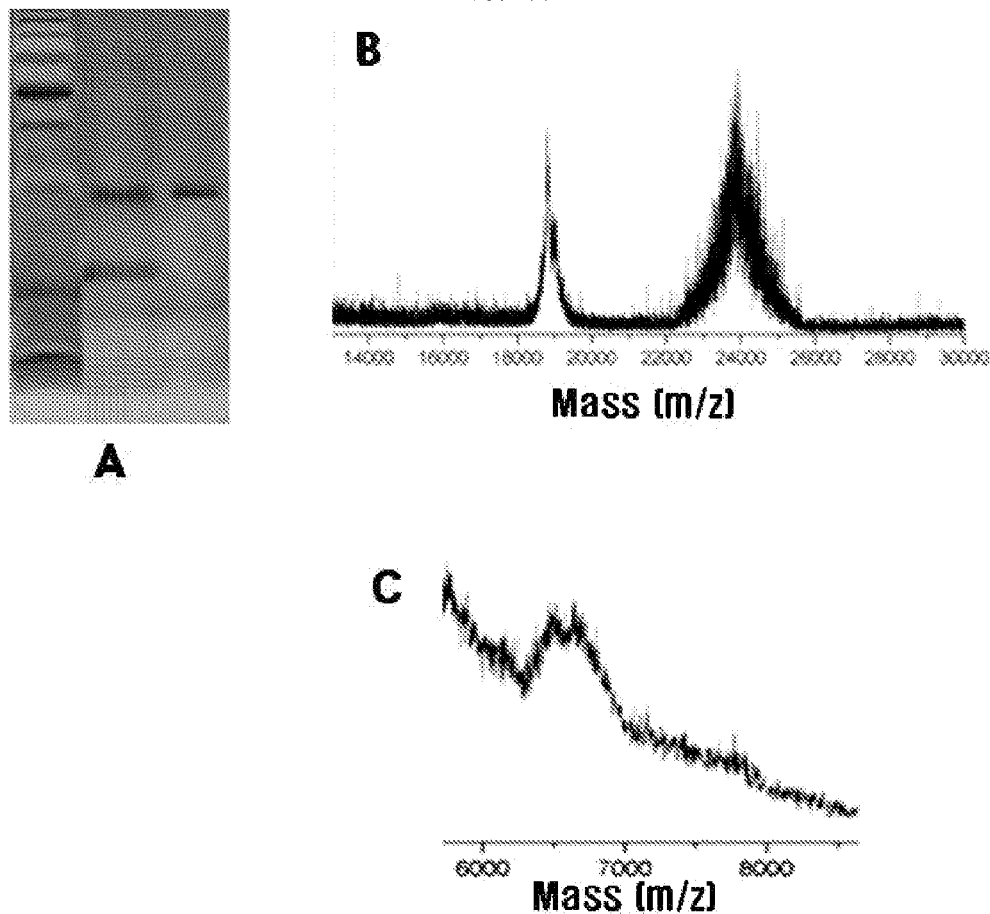
FIG. 11 shows SDS-PAGE results for succinimidyl succinate-PEG-G-CSF (lane 2) and catechol-PEG-G-CSF (lane 3) (FIG. 11A), MALDI-TOF results for tryptic digests of G-CSF (MW: 1792.

The results of the analysis are shown in FIG. 11.

As can be seen in FIG. 11A, in the mono-PEGylated conjugate prepared using mPEG-CT, only the bands of G-CSF and mono-PEGylated G-CSF could be observed (lane 2), and when purifying the conjugate by FPLC, only the mono-PEGylated G-CSF could be separated (lane 3). Accordingly, it was confirmed that the G-CSF protein was mono-PEGylated.

(3) Examination of mono-PEGylation at N-terminal by Tryptic Digestion

PEGylation sites were examined by tryptic digestion of G-CSF and PEG-G-CSF according to the same method as Example 4-(3).

As a result, as shown in FIG. 11B, the results of MALDI-TOF of tryptic digests of G-CSF indicated that the molecular weight of the T1 fragment was 1792. Meanwhile, as shown in FIG. 11C, MALDI-TOF results for tryptic digests of the catechol-PEG-G-CSF indicated that the molecular weight of the T1 fragment was 6792. Thus, it is believed that the above result is the sum of the T1 fragment and PEG (MW: 5000), suggesting that the catechol-PEG derivative was mono-conjugated with the protein, unlike the succinimidyl succinate-PEG derivative.

Through Examples 1 to 5 above, the polyethylene glycol derivative (PEG-CT) having the compound containing a catechol bound thereto was successfully synthesized, and it was confirmed that, when the PEG-CT derivative is conjugated with protein or peptide, it can be site-specifically conjugated with the N-terminal of the protein or peptide.

Example 6

Increase in PEGylation Efficiency Using Sodium Periodate

To increase PEGylation efficiency, the oxidizing agent sodium periodate was used. Under a low pH condition, the ratio of alpha amines (N-terminal amines) present in the form of $NH_3+$ cations is higher than that of epsilon amines (lysine residue amines). Thus, only the N-terminal amine can react with a quinone oxidized by periodate. Accordingly, PEGylation was performed under conditions of varying sodium periodate ratios.

5 mg of lysozyme and 5 mg of mPEG-CT were dissolved in a buffer (pH 6.0) and allowed to react at 4° C. for 720 minutes. At this time, sodium periodate was added at ratios of 0:1, 0.5:1, and 1:1, and 2:1 relative to mPEG-CT.

An experiment on a control group was performed in the same manner as Example 3-(2).

Figure 12:
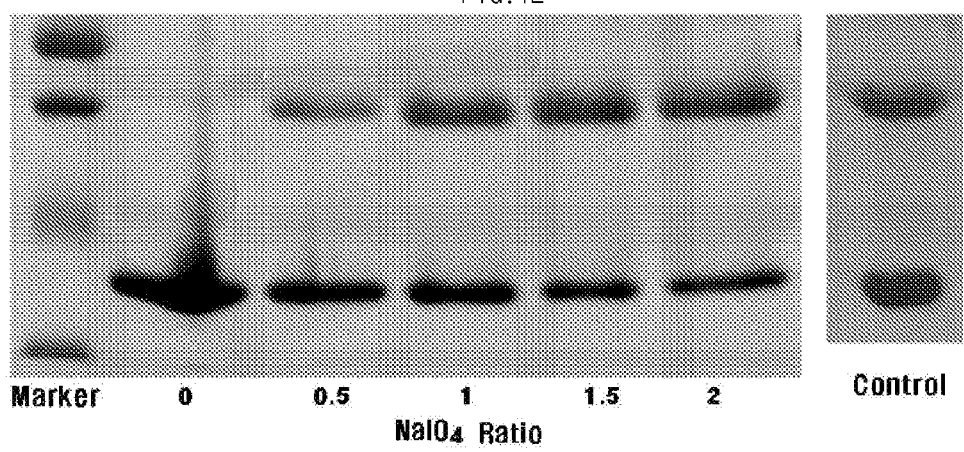
FIG. 12 is a set of SDS-PAGE gel photographs showing the results of adding $NaIO_4$ at ratios of 0:1, 0.5:1, 1:1, 1.5:1, and 2:1 relative to catechol at pH 6.0 during the PEGylation reaction of lysozyme protein.
Figure 13:
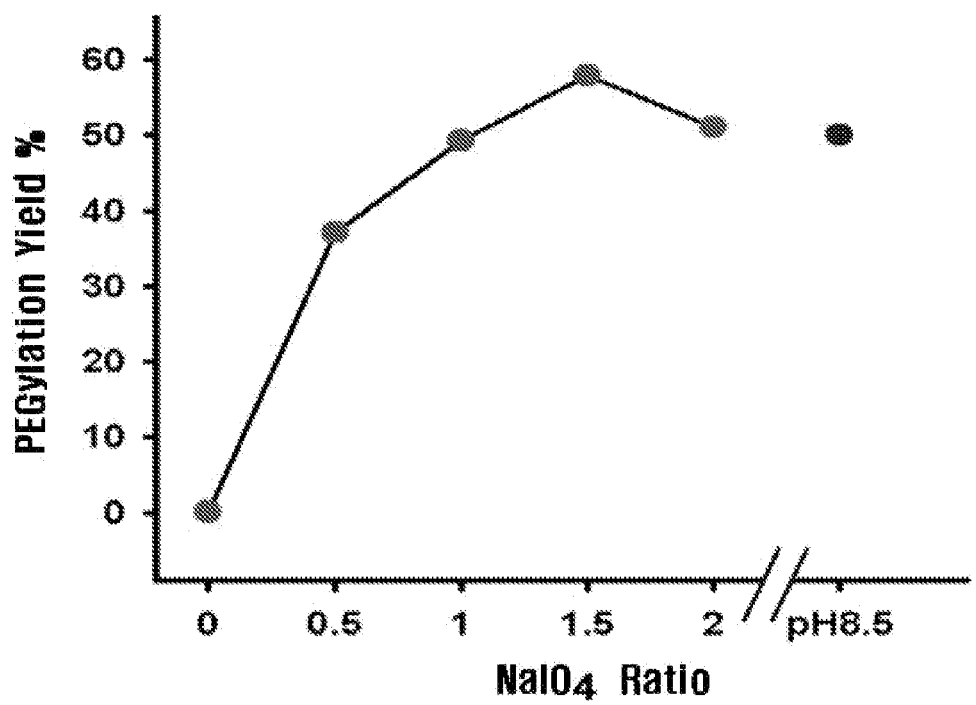
FIG. 13 is a graphic diagram showing relative values of PEGylation yield when adding $NaIO_4$ at ratios of 0:1, 0.5:1, 1:1, 1.5:1, and 2:1 relative to catechol at pH 6.0 during the PEGylation reaction of lysozyme protein.

The experimental results are comparatively shown in FIGS. 12 and 13 which show PEGylation efficiencies at different periodate ratios at a pH of 6.0 or below. The last column of the SDS-PAGE gel and the PEGylation yield value at a pH of 8.5 in the graph are the results for the control group that underwent no chemical reaction. The experimental results indicated that the highest yield was 57.94% at a periodate: catechol ratio of 1.5:1.

Example 7

Examination of In Vivo Duration Time of PEG-EPO Conjugate (1) Preparation and Confirmation of PEG-EPO Conjugate Using mPEG-CT or mPEG-SS Erythropoietin (MW: 30 kDa) is a hormone that is produced in the kidneys and stimulates the production of erythrocytes in the marrow. The most important function is to stimulate the differentiation and development of erythrocytes. In this Example, mPEG-CT (MW: 30 kDa) was used, because PEGylation that attaches a PEG of at least 20 kDa could be effective in an in vivo environment.

A PEG-EPO conjugate was prepared according to the same methods as described in Examples 2-(1) and 3-(1), except that sodium periodate was added at a ratio of 1.5:1 during the reaction of mPEG-CT with EPO and that a pH of 7.5 was used. Because proteins have different pKa values, the pH that was somewhat higher than in the case of lysozyme was used. After completion of the reaction, the PEG-conjugated EPO was purified using a FPLC system (Shephacryl™ Hiprep 26/60 S-200-HR 320 ml).

Figure 14:
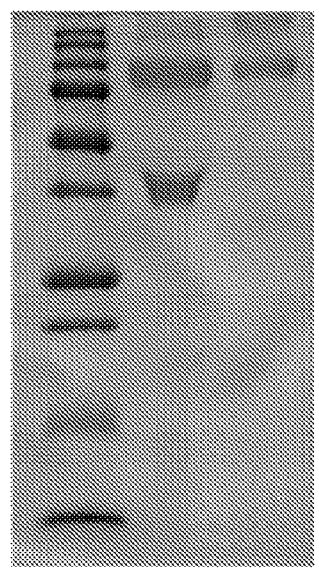
FIG. 14 shows the results of SDS-PAGE of a mixture resulting from the reaction of mPEG-CT with EPO (lane 2; two bands) and of mPEG-CT-EPO (PEG-EPO; lane 3; one band) purified using a FPLC system.
Figure 15:
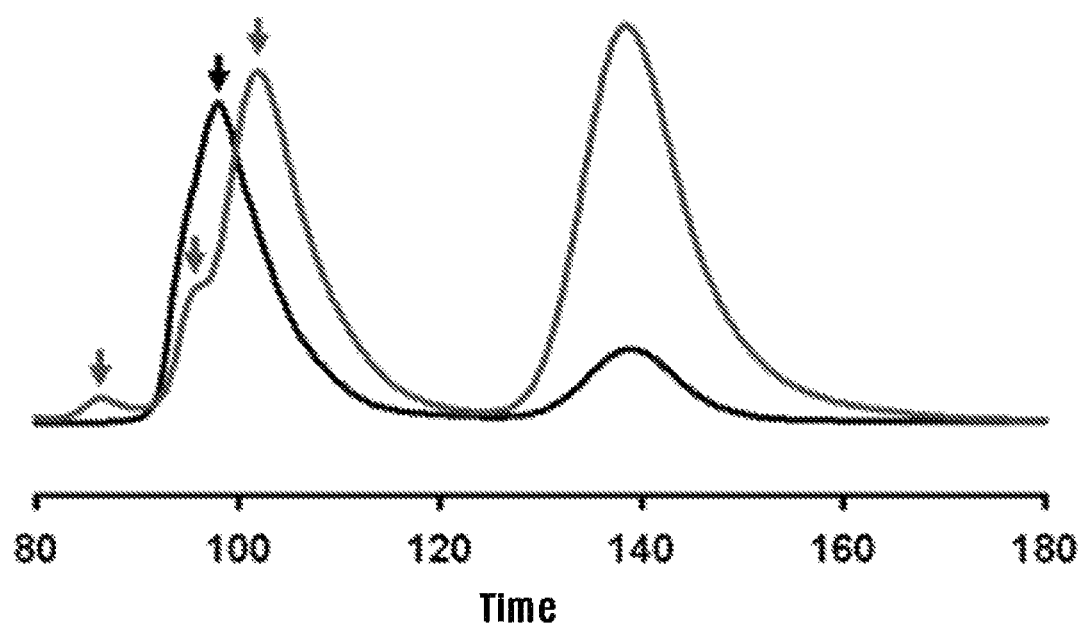
FIG. 15 is a graphic diagram showing the results of RP-HPLC.

The analysis results are shown in FIGS. 14 and 15. As can be seen from the results of SDS-PAGE gel analysis, after the FPLC process, the EPO mixture (a black line in FIG. 15; 140 minutes) and the mPEG-CT-EPO (PEG-EPO; a second line in FIG. 14 or a black line in FIG. 15; 98 minutes) were completely purified (a third line in FIG. 14). The PEGylation yield was 77%. From the results of MALDI-ToF analysis, a mono-PEGylated EPO could be seen (data not shown).

mPEG-SS (MW: 20 kDa) was used as a protein multi-PEGylation control. A mono-PEGylated EPO was detected at 105 minutes, and a di-PEGylated EPO was detected at 95 minutes and purified by FPLC (a red line in FIG. 15). A peak was detected at 85 minutes, indicating a conjugated protein and a multi-PEGylated protein. The PEGylation yield was much lower in mPEG-SS than mPEG-CT, but it was indicated by an adjusted height in FIG. 15 for the convenience of comparison.

(2) Examination of In Vivo Duration Time

In an in vivo pharmacokinetic study, a multi-PEGylated EPO, that is, a multi-PEGylated PEG-EPO prepared using the mPEG-SS in Example 7-(1), was used as a positive control. Mice were intravenously injected with 100 µg/kg (mouse bodyweight) of EPO, and then the in vivo circulation time of the EPO was measured. For each protein sample, five mice were used, and about 2.5 µg of each protein, was injected into each mouse. This protein amount corresponds to $6.4 \times 10^4$ mIU of EPO when the conversion factor was assumed to be $2.56 \times 10^4$ mIU. The proteins of the plasma were quantified by ELISA, and the quantified amounts were adjusted according to the affinities of different ELISA antibodies against the protein samples, that is, PEG-EPO, multi-PEG-EPO and EPO.

Figure 16:
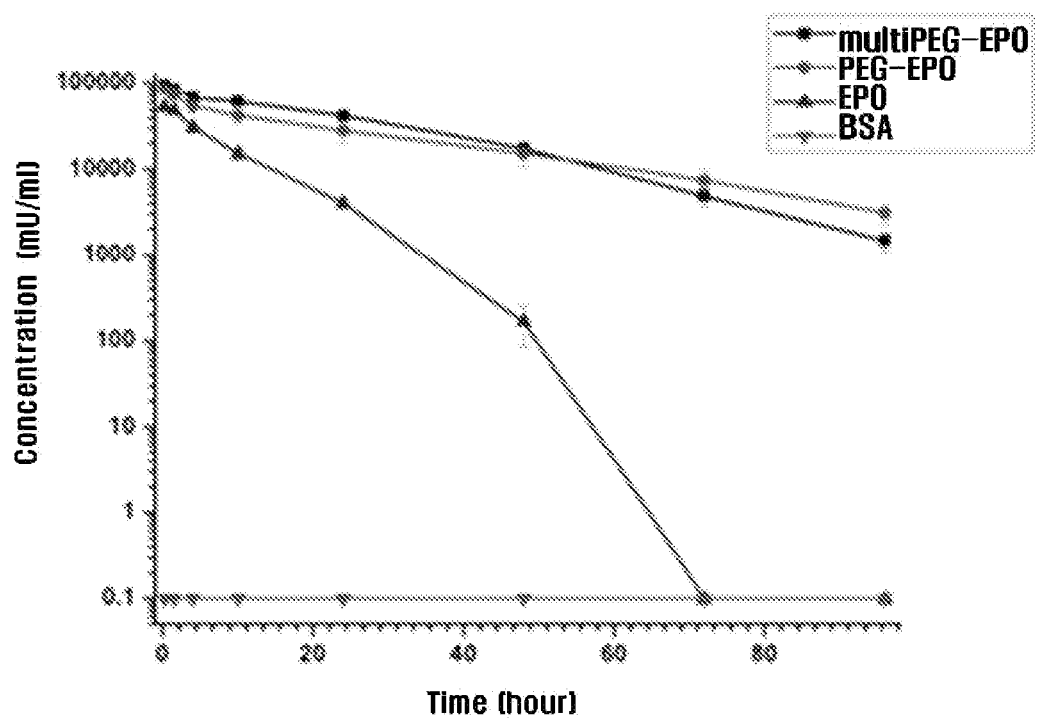
FIG. 16 is a graphic diagram showing the in vivo half-lives of mono-PEG-EPO, multi-PEG-EPO and EPO.

The analysis results are shown in FIG. 16. As can be seen in FIG. 16, the half-lives of all the protein samples were measured to be about 4-96 hours. At the initial stage (0.25-4 hours), similar tendencies were shown, but were thought to be the results which were somewhat inaccurate for measuring accurate half-lives. During the middle stage (4-48 hours), the EPO circulated and had a half-life of 6 hours. For 72 hours after the injection, the EPO was not detected in the plasma. The multi-PEG-EPO had a longer half-life (30 hours). However, during the late stage (48-96 hours), the multi-PEG-EPO had a shorter half-life (15 hours). On the other hand, the mono-PEG-EPO had the longest half-life (30 hours) and observed for the longest time (96 hours). These results suggest that the multi-PEG-EPO and the mono-PEG-EPO exhibited excellent usual EPO due to the long half-life and that the mono-PEG-EPO had a long half-life compared to the multi-PEG-EPO. Thus, it could be predicted that the mono-PEG-EPO had a long in vivo duration time such that the in vivo efficacy and stability of the protein drug could be maximized.

(3) Measurement of Biological Activity

To measure biological activity, the hematocrit ratio of blood in each sample was measured.

EDTA was added to blood extracted from the mice in order to prevent the blood from coagulating, and then the hematocrit ratio of the blood was measured using VetScan HM5 (Abaxis).

Figure 17:
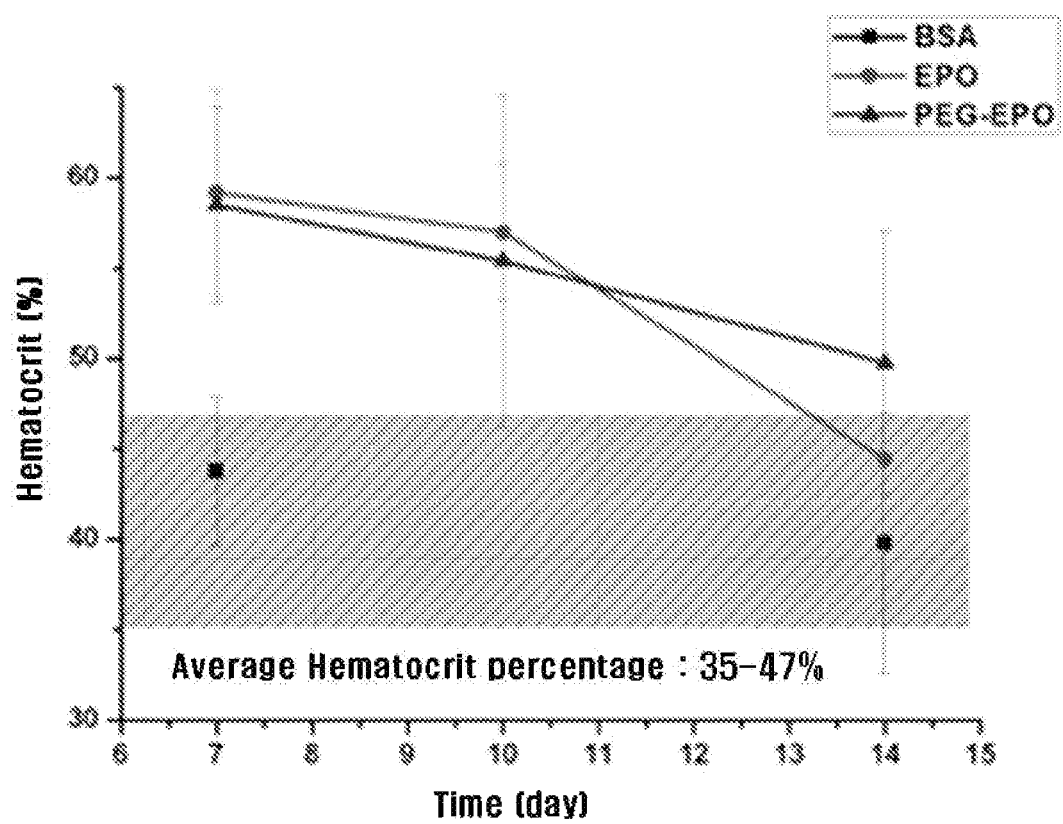
FIG. 17 is a graphic diagram showing the results of measuring the hematocrit ratio of mono-PEG-EPO and EPO.

As a result, as shown in FIG. 17, during 0 to 3 days after the injection, EPO and PEG-EPO had similar activities, and such similar activities were also shown even 7-10 days after the injection. However, the EPO lost most of its in vivo activity at day 14, whereas the PEG-EPO still maintained its effect. From these results, it can be predicted that the protein drug of the present invention, which was not chemically modified, has excellent in vivo efficacy.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

Industrial Applicability

According to the present invention, the catechol-PEG derivative can be site-specifically mono-conjugated with the N-terminal amine group of a protein or peptide, so that a homogeneous polyethylene glycol-protein or -peptide conjugate can be obtained in high yield. Unlike the prior art conjugate, the conjugate obtained according to the present invention allows the decrease in the activity of the protein to be minimized without chemically modifying the protein, and thus the conjugate has an excellent pharmacological effect. Also, because the conjugate is homogeneous, the process for preparing the conjugate can be simplified. Moreover, the conjugate has uniform biological efficacy in vivo and shows strong resistance to hydrolysis and thus a long in vivo duration time. Accordingly, the conjugate has the effect of increasing the in vivo efficacy and stability of the protein drug.

The invention claimed is:

1. A conjugate comprising:
a protein or a peptide; and
a polyethylene glycol derivative bound to a compound comprising a catechol of formula 1 end-functionalized at a first side, and at least one moiety selected from the group consisting of a carboxyl group, an amine group, a hydroxyl group, and an aldehyde group at a second side, wherein the protein or the peptide is site-specifically mono-PEGylated at an N-terminal amine group with the catechol of the polyethylene glycol derivative:

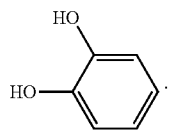

[Formula 1]

2. The conjugate of a protein or a peptide with a polyethylene glycol derivative according to claim 1, wherein the polyethylene glycol is any one selected from the group consisting of methoxy polyethylene glycol aldehyde, polyethylene glycol succinimidyl propionate, methoxy polyethylene glycol succinimidyl butanoate, methoxy polyethylene glycol succinimidyl succinate, methoxy polyethylene glycol benzotriazole carbonate, methoxy polyethylene glycol epoxide, methoxy polyethylene glycol carbonylimidazole, methoxy polyethylene glycol p-nitrophenyl carbonate, methoxy polyethylene glycol isocyanate, methoxy polyethylene glycol amine containing primary amine, methoxy polyethylene glycol hydrazide, and methoxy carboxyl polyethylene glycol containing carboxyl groups.

3. The conjugate of a protein or a peptide with a polyethylene glycol derivative according to claim 1, wherein the polyethylene glycol is any one shape selected from the group consisting of linear shape, branch shape, brush shape and star-like shape.

4. The conjugate of a protein or a peptide with a polyethylene glycol derivative according to claim 3, wherein the compound containing a catechol is any one selected from the group consisting of 3,4-dihydroxy-L-phenylalanine containing carboxyl and amine groups, 3-hydroxy-tyramine containing amine groups, 3,4-dihydroxyhydrocinnamic acid containing carboxyl groups, 3,4-dihydroxybenzaldehyde containing aldehyde groups and norepinephrine.

5. The conjugate of a protein or a peptide with a polyethylene glycol derivative according to claim 1, wherein the molecular weight of the compound containing a catechol is 1,000 Da or less.

6. The conjugate of a protein or a peptide with a polyethylene glycol derivative according to claim 1, wherein the molecular weight of the polyethylene glycol is 500 to 100,000 Da.

7. The conjugate of a protein or a peptide with a polyethylene glycol derivative according to claim 1, wherein the protein is any one selected from the group consisting of lysozyme, basic fibroblast growth hormone (bFGF), granulocyte colony-stimulating factor (GCSF), erythropoientin (EPO), epidermal growth factor (EGF), human growth hormone (hGH), interferon (IFN), interleukin-2 (IL-2), vascular endothelial growth factor (VEGF), luteinizing hormone-releasing hormone (LHRH), growth hormone-releasing hormone (GHRH), mammalian urate oxidase (uricase) and arginine deiminase (ADI).

8. The conjugate of a protein or a peptide with a polyethylene glycol derivative according to claim 1, wherein the peptide is any one selected from the group consisting of hinge-7, hinge-3, buforin, histonin, protegrin, indolicidin, histatin, BIP, magainin 2, glucagon-like peptide (GLP-1), GNRH/LHRH agonist, somatostatin analogues, immunoregulatory peptide glatiramer, salmon calcitonin, desmopressin, platelet coagulation inhibitory peptides, eptifibatide, and HIV fusion inhibitor enfuvirtide.

9. A method for preparing a conjugate comprising:
a protein or a peptide; and
a polyethylene glycol derivative bound to a compound comprising a catechol of formula 1 end-functionalized at a first side, and at least one moiety selected from the group consisting of a carboxyl group, an amine group, a hydroxyl group, and an aldehyde group at a second side, wherein the protein or the peptide is site-specifically mono-PEGylated at an N-terminal amine group with the catechol of the polyethylene glycol derivative:

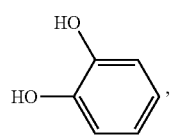

[Formula 1]

the method comprising the steps of:
(a) dissolving the protein or the peptide in a reactor;
(b) dissolving the polyethylene glycol derivative in another reactor; and
(c) adding to and reacting with the solution of step (b) the solution of step (a).

10. The method for preparing a conjugate of a protein or a peptide with a polyethylene glycol derivative according to claim 9, wherein the polyethylene glycol is any one selected from the group consisting of methoxy polyethylene glycol aldehyde, polyethylene glycol succinimidyl propionate, methoxy polyethylene glycol succinimidyl butanoate, methoxy polyethylene glycol succinimidyl succinate, methoxy polyethylene glycol benzotriazole carbonate, methoxy polyethylene glycol epoxide, methoxy polyethylene glycol carbonylimidazole, methoxy polyethylene glycol p-nitrophenyl carbonate, methoxy polyethylene glycol isocyanate, methoxy polyethylene glycol amine containing primary amine, methoxy polyethylene glycol hydrazide, and methoxy carboxyl polyethylene glycol containing carboxyl groups.

11. The method for preparing a conjugate of a protein or a peptide with a polyethylene glycol derivative according to claim 9, wherein the compound containing a catechol is any one selected from the group consisting of 3,4-dihydroxy-L-phenylalanine containing carboxyl and amine groups, 3-hydroxy-tyramine containing amine groups, 3,4-dihydroxyhydrocinnamic acid containing carboxyl groups, 3,4-dihydroxybenzaldehyde containing aldehyde groups, and norepinephrine.

12. The method for preparing a conjugate of a protein or a peptide with a polyethylene glycol derivative according to claim 9, wherein the method further comprises step (d) of dialyzing the solution of step (c) and then separating the conjugate from the dialyzed solution.

13. The method for preparing a conjugate of a protein or a peptide with a polyethylene glycol derivative according to claim 12, wherein the step (d) is separating the conjugate through liquid phase chromatography.

14. The method for preparing a conjugate of a protein or a peptide with a polyethylene glycol derivative according to claim 9, wherein the step (b) is dissolving the polyethylene glycol derivative with an oxidizing agent at a molar ratio of 1:1 to 1:10 relative to the polyethylene glycol derivative in the reactor.

15. The method for preparing a conjugate of a protein or a peptide with a polyethylene glycol derivative according to claim 14, wherein the oxidizing agent is any one or more selected from the group consisting of $NaIO_4$, $MnCl_2$, $FeCl_2$, $FeCl_3$, $KMnO_4$, $H_2O_2$, $Na_2Cr_2O_7$, and $Na_3VO_4$.

16. The method for preparing a conjugate of a protein or a peptide with a polyethylene glycol derivative according to claim 9, wherein the step (b) is carried out at 4 to 25 ° C. for 2 to 100 hours.

* * * * *